(12) United States Patent
He et al.

(10) Patent No.: US 12,150,814 B2
(45) Date of Patent: Nov. 26, 2024

(54) ULTRASONIC SIGNAL PROCESSING METHOD AND APPARATUS, DEVICE AND STORAGE MEDIUM

(71) Applicant: Wuxi Hisky Medical Technologies Co., Ltd., Wuxi (CN)

(72) Inventors: Qiong He, Wuxi (CN); Jinhua Shao, Wuxi (CN); Jin Sun, Wuxi (CN); Houli Duan, Wuxi (CN)

(73) Assignee: Wuxi Hisky Medical Technologies Co., Ltd., Wuxi (CN)

( * ) Notice: Subject to any disclaimer, the term of this patent is extended or adjusted under 35 U.S.C. 154(b) by 380 days.

(21) Appl. No.: 17/585,311

(22) Filed: Jan. 26, 2022

(65) Prior Publication Data

US 2022/0142615 A1    May 12, 2022

Related U.S. Application Data

(63) Continuation of application No. PCT/CN2020/105021, filed on Jul. 28, 2020.

(30) Foreign Application Priority Data

Aug. 1, 2019    (CN) .......................... 201910706466.6

(51) Int. Cl.
*A61B 8/00*    (2006.01)
*A61B 8/08*    (2006.01)
(Continued)

(52) U.S. Cl.
CPC .......... *A61B 8/5223* (2013.01); *G06T 7/0012* (2013.01); *G16H 30/40* (2018.01);
(Continued)

(58) Field of Classification Search
CPC ..... A61B 8/5223; A61B 8/0825; A61B 8/483; A61B 8/5207; A61B 8/085; A61B 8/00;
(Continued)

(56) References Cited

U.S. PATENT DOCUMENTS

2013/0023767 A1    1/2013    Mammone
2017/0296150 A1    10/2017    Rosenzweig
(Continued)

FOREIGN PATENT DOCUMENTS

CN        1723856 A       1/2006
CN       103040487 A      4/2013
(Continued)

OTHER PUBLICATIONS

First Office Action of the priority CN application.
(Continued)

*Primary Examiner* — Qian Yang
(74) *Attorney, Agent, or Firm* — J.C. PATENTS

(57) ABSTRACT

An ultrasonic signal processing method and apparatus (30), a computer device (50) and a storage medium. The method includes: acquiring a target ultrasonic signal of a dynamic broadband corresponding to target tissue (101); determining, according to the target ultrasonic signal, an acoustic characteristic parameter of the target tissue (102); performing assessment processing to the target tissue according to the acoustic characteristic parameter of the target tissue (103). The acoustic characteristic parameter of the target tissue is determined according to the target ultrasonic signal of the dynamic broadband corresponding to the target tissue, and the assessment is performed to the target tissue based on the acoustic characteristic parameter of the target tissue, and ultrasonic signals of the target tissue at multiple frequencies are comprehensively considered, so that signal components are varied, thereby improving accuracy of the assessment to the target tissue.

17 Claims, 2 Drawing Sheets

(51) Int. Cl.
  *G06T 7/00* (2017.01)
  *G16H 30/40* (2018.01)
(52) U.S. Cl.
  CPC ... *A61B 8/0825* (2013.01); *G06T 2207/10132* (2013.01); *G06T 2207/30056* (2013.01); *G06T 2207/30068* (2013.01)
(58) Field of Classification Search
  CPC .............. A61B 8/0858; G06T 7/0012; G06T 2207/10132; G06T 2207/30056; G06T 2207/30068; G16H 30/40; G01S 15/8954
  See application file for complete search history.

(56) References Cited

U.S. PATENT DOCUMENTS

| | | |
|---|---|---|
| 2019/0008485 A1 | 1/2019 | Li |
| 2019/0082964 A1 | 3/2019 | Byrnes |

FOREIGN PATENT DOCUMENTS

| | | |
|---|---|---|
| CN | 103575810 A | 2/2014 |
| CN | 103637820 A | 3/2014 |
| CN | 103687549 A | 3/2014 |
| CN | 105193455 A | 12/2015 |
| CN | 107303186 A | 10/2017 |
| CN | 107647881 A | 2/2018 |
| CN | 108685596 A | 10/2018 |
| CN | 109044407 A | 12/2018 |
| CN | 110313936 A | 10/2019 |
| CN | 110313937 A | 10/2019 |
| CN | 110368023 A | 10/2019 |
| JP | 2004321582 A | 11/2004 |
| JP | 2011224410 A | 11/2011 |
| JP | 2013515587 A | 5/2013 |
| JP | 2013244219 A | 12/2013 |
| JP | 2017012427 A | 1/2017 |
| RU | 2210409 C2 | 8/2003 |
| RU | 2567268 C2 | 11/2015 |
| RU | 2654608 C2 | 5/2018 |
| WO | WO2018019791 A1 | 2/2018 |

OTHER PUBLICATIONS

Second Office Action of the priority CN application.
International Search Report of PCT/CN2020/105021.
NPL: "Study on the Frequency Property of Ultrasonic Scatterer in Soft Tissue", Piezoelectrics & Acoustooptics, vol. 33 No. 5, Oct. 2011.
First Office Action of the parallel application JP2022-504146.
Extended European Search Report of the parallel application EP20846789.4.
First Office Action of the parallel application RU2022102112.

ULTRASONIC SIGNAL PROCESSING METHOD AND APPARATUS, DEVICE AND STORAGE MEDIUM

CROSS-REFERENCE TO RELATED APPLICATIONS

This application is a continuation of International Application No. PCT/CN2020/105021, filed on Jul. 28, 2020, which claims priority to Chinese Patent Application No. 201910706466.6, filed on Aug. 1, 2019. The disclosures of the aforementioned applications are hereby incorporated by reference in their entireties.

TECHNICAL FIELD

The present application relates to the technical field of ultrasonic technology, and in particular, to an ultrasonic signal processing method and apparatus, a device and a storage medium.

BACKGROUND

As the development of science and technology, ultrasonic imaging technology is broadly used in various fields, and is applied in clinical diagnose due to its advantages such as real-time, low-cost, non-invasive and non-ionizing radiation. Quantitative ultrasound can provide quite intuitive quantitative assessment for clinicians, such as elasticity and blood flow.

However, quantitative ultrasound is related to signal characteristics of the ultrasound itself, and is easy to be interfered by other signals in tissue or around. Therefore, how to accurately determine the state of target tissue by adopting the ultrasonic technology becomes an urgent technical problem.

SUMMARY

The present application provides an ultrasonic signal processing method and apparatus, a device and a storage medium, to solve the drawbacks in the prior art that the state of target tissue is not accurately determined.

A first aspect of the present application provides an ultrasonic signal processing method, including:
  acquiring a target ultrasonic signal of a dynamic broadband corresponding to target tissue;
  determining an acoustic characteristic parameter of the target tissue according to the target ultrasonic signal; and
  performing assessment processing to the target tissue according to the acoustic characteristic parameter of the target tissue.

A second aspect of the present application provides an ultrasonic signal processing apparatus, including:
  an acquiring model, configured to acquire a target ultrasonic signal of a dynamic broadband corresponding to target tissue;
  a determining model, configured to determine an acoustic characteristic parameter of the target tissue according to the target ultrasonic signal; and
  a processing module, configured to perform assessment processing to the target tissue according to the acoustic characteristic parameter of the target tissue.

A third aspect of the present application provides a computer device, including: at least one processor and a memory;
the memory stores a computer program; the at least one processor executes the computer program stored in the memory to implement the method provided in the first aspect.

A fourth aspect of the present application provides a computer-readable storage medium, where the computer-readable storage medium stores a computer program, and the computer program, when being executed, implements the method provided in the first aspect.

The present application provides an ultrasonic signal processing method and apparatus, a device and a storage medium, where an acoustic characteristic parameter of target tissue is determined according to a target ultrasonic signal of a dynamic broadband corresponding to the target tissue, and an assessment is performed to the target tissue based on the acoustic characteristic parameter of the target tissue. Ultrasonic signals of the target tissue at multiple frequencies are comprehensively considered, so that signal components are varied, thereby improving accuracy of the assessment to the target tissue.

BRIEF DESCRIPTION OF DRAWINGS

In order to explain the embodiments of the present application or the technical solutions in the prior art more clearly, the following will briefly introduce the drawings that need to be used in the description of the embodiments or the prior art. Obviously, the drawings in the following description are some embodiments of the present application, and for those of ordinary skills in the art, other drawings can be obtained according to these drawings without making creative efforts.

Figure 1:
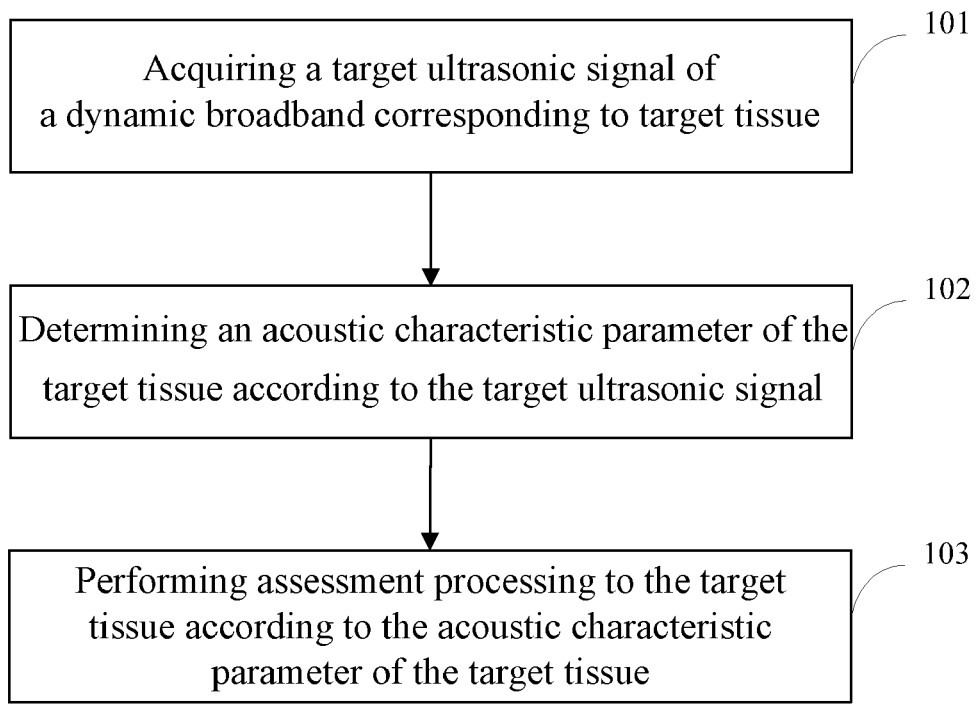
FIG. 1 is a schematic flow chart of an ultrasonic signal processing method provided in an embodiment of the present application.
Figure 2:
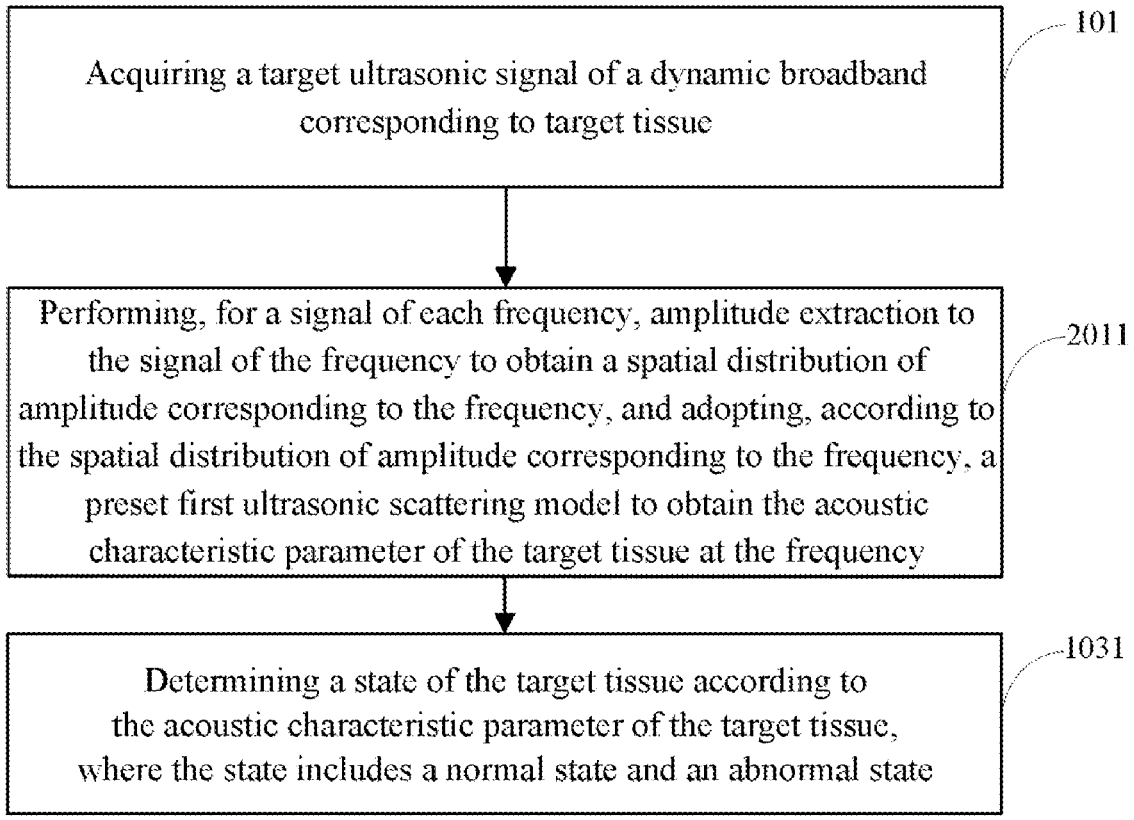
FIG. 2 is a schematic flow chart of an ultrasonic signal processing method provided in another embodiment of the present application.

Through the above drawings, specific embodiments of the present application have been shown, which will be described in more detail later. These drawings and text descriptions are not intended to limit the scope of the concept of the present application in any way, but to explain the concept of the present application to those skilled in the art by referring to specific embodiments.

DESCRIPTION OF EMBODIMENTS

In order to make the purpose, technical solution and advantages of the embodiments of the present application clearer, the technical solution in the embodiments of the present application will be clearly and completely described below with reference to the drawings in the embodiments of the present application. Obviously, the described embodiments are part of embodiments of the present application, rather than all of them. Based on the embodiments in the present application, all other embodiments obtained by those of ordinary skills in the art without making creative efforts are within the protection scope of the present application.

The ultrasonic signal processing method provided in the embodiments of the present application is adapted to a scenario where target tissue is detected by adopting a dynamic broadband probe to obtain an ultrasonic signal of the dynamic broadband of the target tissue, and a state of the target tissue is determined based on the ultrasonic signal of the dynamic broadband of the target tissue. The target tissue may be liver tissue, muscle tissue, adipose tissue, breast tissue, thyroid tissue and other tissue, which is not specifically limited. The state of the target tissue may be a normal state or a pathological state, and if the state is the pathological state, it may further include a pathological type and a corresponding pathological level. Taking the liver tissue as an example, the pathological state includes fatty liver, tumor, etc., and the fatty liver may include mild fatty liver, moderate fatty liver and severe fatty liver, etc. The specific pathological level may be set according to actual demand, and is not limited in the embodiments of the present application.

In addition, the terms such as "first", "second" are only used for descriptive purposes, and cannot be understood as indicating or implying relative importance or implicitly indicating the number of indicated technical features. In the description of the following embodiments, "multiple" refers to two or more than two, unless otherwise specifically defined.

The following specific embodiments can be combined with each other, and the same or similar concepts or processes may not be repeated in some embodiments. Embodiments of the present application will be described below with reference to the accompanying drawings.

First Embodiment

The present embodiment provides an ultrasonic signal processing method used to process an ultrasonic signal of a dynamic broadband, to determine a state of target tissue. An executive entity of the present embodiment is an ultrasonic signal processing apparatus, and the apparatus may be provided in a computer device.

FIG. 1 shows a schematic flow chart of an ultrasonic signal processing method provided in the present embodiment, the method including:

Step 101, acquiring a target ultrasonic signal of a dynamic broadband corresponding to target tissue.

Specifically, the target tissue can be detected by a dynamic broadband ultrasonic probe, to obtain an original ultrasonic signal of the dynamic broadband, and the original ultrasonic signal is processed to obtain the target ultrasonic signal of the dynamic broadband corresponding to the target tissue.

The dynamic broadband refers to that the ultrasonic probe can work in a relatively wide signal band range, and a center frequency of the probe is dynamically adjustable. Specifically, the broadband generally refers to that a ratio between a signal frequency range, in which the ultrasonic probe can work, and the center frequency, is greater than or equal to 60%. The target ultrasonic signal of the dynamic broadband refers to an ultrasonic signal obtained by adopting the broadband probe to detect the target tissue under the excitation of different center frequencies.

Illustratively, in medical field, a ratio between a bandwidth of the ultrasonic probe and the center frequency is greater than or equal to 60%, and signal frequencies of 0.1 MHz-100 MHz are involved. Certainly, it is not limited to the ultrasonic probe of such frequency range, and may also be the ultrasonic probe of other range, for example, for aerial or geological aspects, the frequency includes 20 Hz-0.5 MHz. For example, the frequency range of the ultrasonic probe is 1 MHz-10 MHz, then the bandwidth of the ultrasonic probe is 9 MHz, and if the center frequency is 5 MHz, then the ratio between the bandwidth of the ultrasonic probe and the center frequency is 9/5*100%=180%.

The target tissue may be human or animal tissue such as liver tissue, muscle tissue, adipose tissue, breast tissue or thyroid tissue, or tissue in aerial or geological aspects, which is not limited in the present embodiment.

The ultrasonic probe is connected to an ultrasonic imaging apparatus, to realize collection of an ultrasonic echo signal or a transmitted wave signal of the target tissue, which is referred to as the original ultrasonic signal in the embodiments of the present application. The original ultrasonic signal may be one-dimensional, two-dimensional or three-dimensional, which is set according to actual demand. The ultrasonic imaging apparatus may include a transmitting apparatus, a receiving apparatus and an image processing apparatus, etc. Since the ultrasonic probe is a dynamic broadband ultrasonic probe, the collected original ultrasonic signal includes at least signals of two frequencies.

Optionally, data calibration may be performed to the original ultrasonic signal to obtain the target ultrasonic signal. The data calibration needs to be performed to the original ultrasonic signal because the collected original ultrasonic signal is influenced by directivity of the ultrasonic probe, focusing configuration or setting of the probe, sensitivity of the probe, system gain and other signal processing manners, etc.

Optionally, a component of interest may also be extracted from the original ultrasonic signal, and extracting the component of interest specifically refers to extract information of interest from the original ultrasonic signal. For example, when detecting the liver tissue, the obtained original ultrasonic signal may include an ultrasonic signal of subcutaneous tissue and an ultrasonic signal of the liver tissue, and the ultrasonic signal of the liver tissue needs to be extracted from the original ultrasonic signal. For another example, the original ultrasonic signal includes the frequency range of 1-20 MHz, and according to actual experience, high frequency would have been severely attenuated when arriving at the target tissue, thus would not have effective function. The ultrasonic signal within a range of 1-5 MHz may be extracted from the original ultrasonic signal to act as the target ultrasonic signal, etc. Processing can be performed according to actual circumstances, which is not limited in the present embodiment.

After the original ultrasonic signal is collected, the target ultrasonic signal of the dynamic broadband corresponding to the target tissue may be obtained after certain processing.

Optionally, after the original ultrasonic signal is obtained, signals of different frequencies of the original ultrasonic signal may be obtained by means of frequency filtering or wavelet decomposition or the like.

Step 102, determining an acoustic characteristic parameter of the target tissue according to the target ultrasonic signal.

Specifically, after the target ultrasonic signal of the dynamic broadband corresponding to the target tissue is obtained, the acoustic characteristic parameter of the target tissue may be obtained according to the target ultrasonic signal.

The acoustic characteristic parameter may include at least one of a scattering coefficient, a scatterer size, a scatterer distribution feature, comprehensive information, amplitude variation, frequency variation and other related parameters. The amplitude variation refers to amplitude characteristics at different positions, and the frequency variation refers to frequency characteristics at different positions.

Optionally, amplitude extraction may be performed to the signal of each frequency in the target ultrasonic signal to obtain a spatial distribution of amplitude or a histogram corresponding to the frequency, and a preset ultrasonic scattering model is adopted to obtain the acoustic characteristic parameter of the target tissue. The preset ultrasonic scattering model may be any ultrasonic scattering models that can be implemented in the prior art, which will not be repeated herein.

Optionally, a set of acoustic characteristic parameters may be generated for the signal of each frequency. The state of the target tissue may be determined by comprehensively considering a plurality of sets of acoustic characteristic parameters corresponding to a plurality of frequencies.

Optionally, for the signal of each frequency, when processing such as amplitude extraction and model estimation is performed to obtain the acoustic characteristic parameter, the processing may be performed by taking the signal of the frequency as a whole, or by partitioning the signal of the frequency, and the obtained acoustic characteristic parameter may be one value or a set of values, which can be set according to actual circumstances, and is not limited in the present embodiment.

Optionally, the target ultrasonic signal may also be a B-mode ultrasonic signal of the target tissue, where the B-mode ultrasonic signal may be obtained by performing demodulation or grey-level transformation to the original ultrasonic signal, or may be directly obtained from a commercial machine, which can be selected according to actual demand and is not limited in the present embodiment.

The acoustic characteristic parameter of the target tissue may be determined according to the B-mode ultrasonic signal of the target tissue and the preset ultrasonic scattering model.

Step 103, performing assessment processing to the target tissue according to the acoustic characteristic parameter of the target tissue.

Specifically, after the acoustic characteristic parameter of the target tissue is determined, assessment processing may be performed to the target tissue according to the acoustic characteristic parameter of the target tissue.

Optionally, reference characteristic parameters corresponding to various states of different tissues may be acquired in advance, and the acoustic characteristic parameter of the target tissue may be compared with the reference characteristic parameters of the tissue to determine a state to which the target tissue belongs. The state of the tissue may include a normal state and an abnormal state, and the abnormal state may be divided into one or more abnormal types, and each abnormal type corresponds to one or more abnormal levels. The abnormal level embodies degree of abnormality. The abnormal type represents a type of abnormality which is produced to the tissue, for example, the abnormal type of the liver tissue includes fatty liver, tumor, etc., and the abnormal level corresponding to the fatty liver includes mild fatty liver, moderate fatty liver and severe fatty liver, etc. The specific abnormal type and the abnormal level may be set according to actual circumstances of different tissues, and are not limited in the present embodiment.

Illustratively, taking the liver tissue as an example of the target tissue, a reference characteristic parameter or a range of the reference characteristic parameter corresponding to the normal state of the liver tissue, and a reference characteristic parameter or a range of the reference characteristic parameter corresponding to different abnormal levels of different abnormal types of the liver tissue may be acquired in advance, then the acoustic characteristic parameter of the target tissue is compared to the preset range of the reference characteristic parameter, and if the acoustic characteristic parameter of the target tissue belongs to the range of the reference characteristic parameter corresponding to a certain circumstance then the target tissue is determined to belong to the certain circumstance. For example, the acoustic characteristic parameter of the target liver tissue belongs to a range of the reference characteristic parameter corresponding to a normal liver, then the target tissue is determined to be in a normal state, and if the acoustic characteristic parameter of the target liver tissue belongs to a range of the reference characteristic parameter corresponding to the abnormal level of mild fatty liver of the abnormal type of fatty liver, then the target tissue is determined to be a mild fatty liver, and so on. The explanation here is illustrative only, and the specific state and level may be set according to the actual circumstances of different tissues, and is not limited in the present embodiment.

Optionally, a type of tissue may also be identified according to the acoustic characteristic parameter of tissue, for example, the tissue is identified as adipose, muscle, liver, etc. It may also be assessed whether a liver is a fatty liver, whether a muscle is stiff, whether a thyroid is inflamed, whether cancers in various parts are benign or malignant, etc.

In the present embodiment provides an ultrasonic signal processing method, an acoustic characteristic parameter of target tissue is determined according to a target ultrasonic signal of a dynamic broadband corresponding to the target tissue, and an assessment is performed to the target tissue based on the acoustic characteristic parameter of the target tissue. Ultrasonic signals of the target tissue at multiple frequencies are comprehensively considered, so that signal components are varied, thereby improving accuracy of the assessment to the target tissue.

Second Embodiment

The present embodiment further makes supplementary explanation to the method provided in the first embodiment.

As an implementation, on the basis of the above first embodiment, optionally, the target ultrasonic signal includes a signal of at least one frequency. The step 102 specifically includes:

step 2011, performing, for the signal of each frequency, amplitude extraction to the signal of the frequency to obtain a spatial distribution of amplitude corresponding to the frequency, and adopting, according to the spatial distribution of amplitude corresponding to the frequency, a preset first ultrasonic scattering model to obtain the acoustic characteristic parameter of the target tissue at the frequency.

Specifically, the target ultrasonic signal includes signals of at least two frequencies, and signals of different frequencies of the original ultrasonic signal may be obtained by means of frequency filtering or wavelet decomposition or the like. For the signal of each frequency, amplitude extraction is performed to the signal of the frequency to obtain a spatial distribution of amplitude corresponding to the frequency, and according to the spatial distribution of amplitude corresponding to the frequency, a preset first ultrasonic scattering model is adopted to obtain the acoustic characteristic parameter of the target tissue at the frequency. A set of acoustic characteristic parameters may be obtained for the signal of each frequency.

The first ultrasonic scattering model is an ultrasonic scattering model obtained by pre-training with a known spatial distribution of amplitude of an ultrasonic signal of the tissue, and the specific training process is the same as that in the prior art, which will not be repeated here.

The amplitude extraction may be envelope extraction, which is equivalent to signal demodulation, to remove the influence of a carrier signal. The specific extraction manner is known in the prior art, and will not be repeated here.

Optionally, for the signal of each frequency, when processing such as amplitude extraction and model estimation is performed to obtain the acoustic characteristic parameter, the processing may be performed by taking the signal of the frequency as a whole, or by partitioning the signal of the frequency, and the obtained acoustic characteristic parameter may be one value or a set of values, which can be set according to actual circumstances, and is not limited in the present embodiment.

As another implementation, on the basis of the above first embodiment, optionally, the step 102 specifically includes:

step 2021, performing, for a signal of each frequency, amplitude extraction to the signal of the frequency to obtain a histogram corresponding to the signal of the frequency, and adopting, according to the histogram corresponding to the signal of the frequency, a preset second ultrasonic scattering model to obtain the acoustic characteristic parameter of the target tissue at the frequency.

Specifically, the target ultrasonic signal includes signals of at least two frequencies, and signals of different frequencies of the original ultrasonic signal may be obtained by means of frequency filtering or wavelet decomposition or the like. For the signal of each frequency, amplitude extraction is performed to the signal of the frequency to obtain a histogram corresponding to the signal of the frequency, and according to the histogram corresponding to the signal of the frequency, a preset second ultrasonic scattering model is adopted to obtain the acoustic characteristic parameter of the target tissue at the frequency.

The second ultrasonic scattering model is an ultrasonic scattering model obtained by pre-training with a known histogram of an ultrasonic signal of the tissue, and the specific training process is the same as that in the prior art, which will not be repeated here.

As another implementation, on the basis of the above first embodiment, optionally, the acoustic characteristic parameter of the target tissue includes at least one of a scattering coefficient, a scatterer size, a scatterer distribution feature, comprehensive information, amplitude variation and frequency variation.

As another implementation, on the basis of the above first embodiment, optionally, the performing assessment processing to the target tissue according to the acoustic characteristic parameter of the target tissue includes:

step 1031, determining a state of the target tissue according to the acoustic characteristic parameter of the target tissue, where the state includes a normal state and an abnormal state.

Optionally, the abnormal state may include an abnormal type and a corresponding abnormal level.

Specifically, after the acoustic characteristic parameter of the target tissue is determined, reference characteristic parameters corresponding to various states of different tissues may be acquired in advance, and the acoustic characteristic parameter of the target tissue may be compared with a reference characteristic parameter of the type of tissue to determine a state to which the target tissue belongs. The state of the tissue may include a normal state and an abnormal state, and the abnormal state may be divided into one or more abnormal types, and each abnormal type corresponds to one or more abnormal levels. The abnormal level embodies degree of pathology. The abnormal type represents a type of abnormality which is produced to the tissue. For example, the abnormal type of liver tissue includes fatty liver, tumor, etc., and the abnormal level corresponding to the fatty liver includes mild fatty liver, moderate fatty liver and severe fatty liver, etc. The specific abnormal type and the abnormal level can be set according to actual circumstances of different tissues, and are not limited in the present embodiment.

Illustratively, taking the liver tissue as an example of the target tissue, a reference characteristic parameter or a range of the reference characteristic parameter corresponding to the normal state of the liver tissue, and a reference characteristic parameter or a range of the reference characteristic parameter corresponding to different abnormal levels of different abnormal types of the liver tissue may be acquired in advance, then the acoustic characteristic parameter of the target tissue is compared to the preset range of the reference characteristic parameter, and if the acoustic characteristic parameter of the target tissue belongs to a range of a reference characteristic parameter corresponding to a certain circumstance, then the target tissue is determined to belong to the certain circumstance. For example, the acoustic characteristic parameter of the target liver tissue belongs to a range of a reference characteristic parameter corresponding to a normal liver, then the target tissue is determined to be in a normal state, and if the acoustic characteristic parameter of the target liver tissue belongs to a range of a reference characteristic parameter corresponding to the abnormal level of mild fatty liver of the abnormal type of fatty liver, then the target tissue is determined to be mild fatty liver, and so on. The explanation here is illustrative only, and the specific state and level can be set according to the actual circumstances of different tissues, and is not limited in the present embodiment.

Optionally, the state of the tissue may be determined according to the acoustic characteristic parameter of the target tissue at a single frequency, or according to variation of the acoustic characteristic parameter of the target tissue at multiple frequencies, which can be selected according to actual demand and is not limited in the present embodiment.

Illustratively, at the frequency of 3 MHz, a scattering coefficient, a scatterer size and a scatterer distribution feature of the target liver tissue are acquired, and are compared with the pre-acquired reference characteristic parameters of various circumstances of the liver tissue at 3 MHz, to determine the state of the target liver tissue.

Illustratively, at a plurality of frequencies, a plurality of sets of acoustic characteristic parameters of the target liver tissue is acquired, and variation of the acoustic characteristic parameters of the target liver tissue at different frequencies is analyzed, and is compared with the variation of the pre-acquired reference characteristic parameters of the liver tissue at these frequencies to determine the state of the target liver tissue, and so on. The examples will not be listed one by one here.

As another implementation, on the basis of the above first embodiment, optionally, the target ultrasonic signal is B-mode ultrasonic signals corresponding to the target tissue at different frequencies.

The determining an acoustic characteristic parameter of the target tissue according to the target ultrasonic signal includes:

step 2031, for a B-mode ultrasonic signal corresponding to the target tissue at each frequency, adopting a preset third ultrasonic scattering model to obtain the acoustic characteristic parameter of the target tissue at the frequency.

Specifically, the target ultrasonic signal may also be a B-mode ultrasonic signal of the target tissue, where the B-mode ultrasonic signal may be obtained by performing demodulation or grey-level transformation to the original ultrasonic signal, or may be directly obtained from a commercial machine, which can be selected according to actual demand and is not limited in the present embodiment. After the B-mode ultrasonic signal corresponding to the target tissue at each frequency is acquired, the acoustic characteristic parameter of the target tissue may be determined according to the B-mode ultrasonic signal of the target tissue and the preset third ultrasonic scattering model.

The third ultrasonic scattering model is an ultrasonic scattering model obtained by pre-training with a known B-mode ultrasonic signal of the tissue, and the specific training process is the same as that in the prior art, which will not be repeated here.

As another implementation, on the basis of the above first embodiment, optionally, the target tissue is human or animal tissue such as liver tissue, muscle tissue, adipose tissue, breast tissue, thyroid tissue or other tissue, or tissue in aerial or geological aspects, which can be selected according to actual circumstance and is not limited in the present embodiment.

It should be noted that various implementations in the present embodiment may be implemented independently, or may be implemented in any combination when there's no conflict, which is not limited in the present application.

In the present embodiment provides an ultrasonic signal processing method, an acoustic characteristic parameter of target tissue is determined according to a target ultrasonic signal of a dynamic broadband corresponding to the target tissue, and an assessment is performed to the target tissue based on the acoustic characteristic parameter of the target tissue. Ultrasonic signals of the target tissue at multiple frequencies are comprehensively considered, so that signal components are varied, thereby improving accuracy of the assessment to the target tissue.

Third Embodiment

The present embodiment provides an ultrasonic signal processing apparatus, configured to execute the method according to the above first embodiment.

Figure 3:
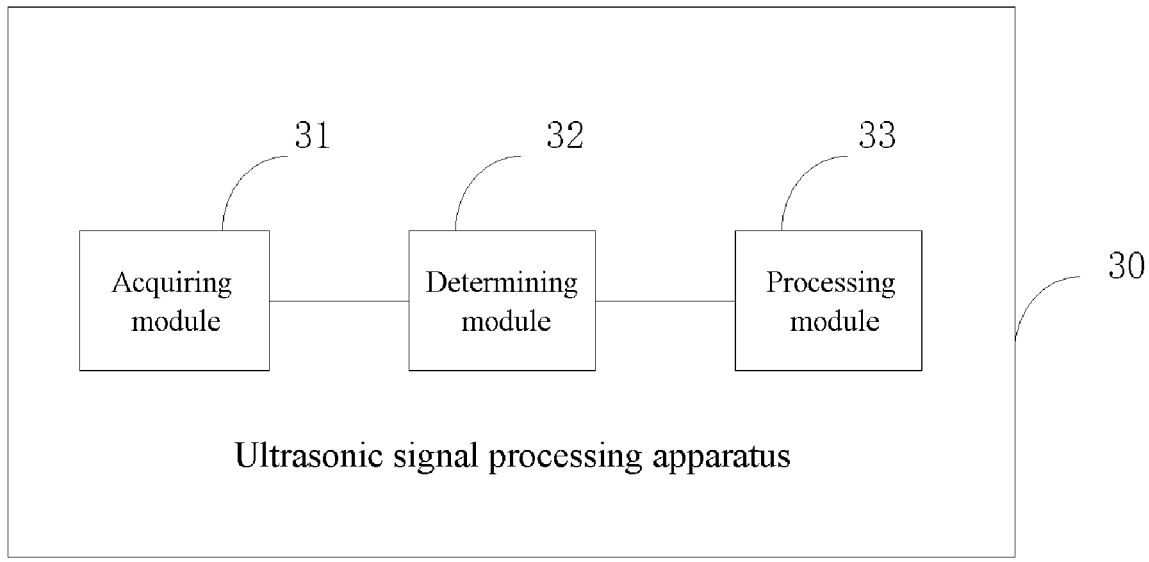
FIG. 3 is a schematic structural diagram of an ultrasonic signal processing apparatus provided in an embodiment of the present application.

FIG. 3 shows a schematic structural diagram of the ultrasonic signal processing apparatus provided in the embodiment of the present application. The ultrasonic signal processing apparatus 30 includes an acquiring module 31, a determining module 32 and a processing module 33.

The acquiring module 31 is configured to acquire a target ultrasonic signal of a dynamic broadband corresponding to target tissue; the determining module 32 is configured to determine an acoustic characteristic parameter of the target tissue; and the processing module 33 is configured to perform assessment processing to the target tissue according to the acoustic characteristic parameter of the target tissue.

With regard to the apparatus in the present embodiment, the specific way in which each module performs operation has been described in detail in the embodiment related to the method, and will not be explained in detail here.

According to the ultrasonic signal processing apparatus provided in the present embodiment, an acoustic characteristic parameter of target tissue is determined according to a target ultrasonic signal of a dynamic broadband corresponding to the target tissue, and an assessment is performed to the target tissue based on the acoustic characteristic parameter of the target tissue. Ultrasonic signals of the target tissue at multiple frequencies are comprehensively considered, so that signal components are varied, thereby improving accuracy of the assessment to the target tissue.

Fourth Embodiment

The present embodiment further provides supplementary explanation to the apparatus provided in the third embodiment to implement the method provided in the second embodiment.

As an implementation, on the basis of the above third embodiment, optionally, the target ultrasonic signal includes a signal of at least one frequency; the determining module is specifically configured to:

perform, for the signal of each frequency, amplitude extraction to the signal of the frequency to obtain a spatial distribution of amplitude corresponding to the frequency, and adopt, according to the spatial distribution of amplitude corresponding to the frequency, a preset first ultrasonic scattering model to obtain the acoustic characteristic parameter of the target tissue at the frequency.

As another implementation, on the basis of the above third embodiment, optionally, the determining module is specifically configured to:

perform, for the signal of each frequency, amplitude extraction to the signal of the frequency to obtain a histogram corresponding to the signal of the frequency, and adopt, according to the histogram corresponding to the signal of the frequency, a preset second ultrasonic scattering model to obtain the acoustic characteristic parameter of the target tissue at the frequency.

As another implementation, on the basis of the above third embodiment, optionally, the acoustic characteristic parameter of the target tissue includes at least one of a scattering coefficient, a scatterer size, a scatterer distribution feature, comprehensive information, amplitude variation and frequency variation.

As another implementation, on the basis of the above third embodiment, optionally, the processing module is specifically configured to:

determine a state of the target tissue according to the acoustic characteristic parameter of the target tissue, where the state includes a normal state and an abnormal state.

As another implementation, on the basis of the above third embodiment, optionally, the target ultrasonic signal is B-mode ultrasonic signals corresponding to the target tissue at different frequencies;

the determining module is specifically configured to:
for a B-mode ultrasonic signal corresponding to the target tissue at each frequency, adopt a preset third ultrasonic scattering model to obtain the acoustic characteristic parameter of the target tissue at the frequency.

As another implementation, on the basis of the above third embodiment, optionally, the target tissue is liver tissue, muscle tissue, adipose tissue, breast tissue or thyroid tissue.

With regard to the apparatus in the present embodiment, the specific way in which each module performs operation has been described in detail in the embodiment related to the method, and will not be explained in detail here.

It should be noted that various implementations in the present embodiment may be implemented independently, or may be implemented in any combination when there's no conflict, which is not limited in the present application.

According to the ultrasonic signal processing apparatus in the present embodiment, an acoustic characteristic parameter of target tissue is determined according to a target ultrasonic signal of a dynamic broadband corresponding to the target tissue, and an assessment is performed to the target tissue based on the acoustic characteristic parameter of the target tissue. Ultrasonic signals of the target tissue at multiple frequencies are comprehensively considered, so that signal components are varied, thereby improving accuracy of the assessment to the target tissue.

Fifth Embodiment

The present embodiment provides a computer device, configured to execute the method provided in the above embodiments.

Figure 4:
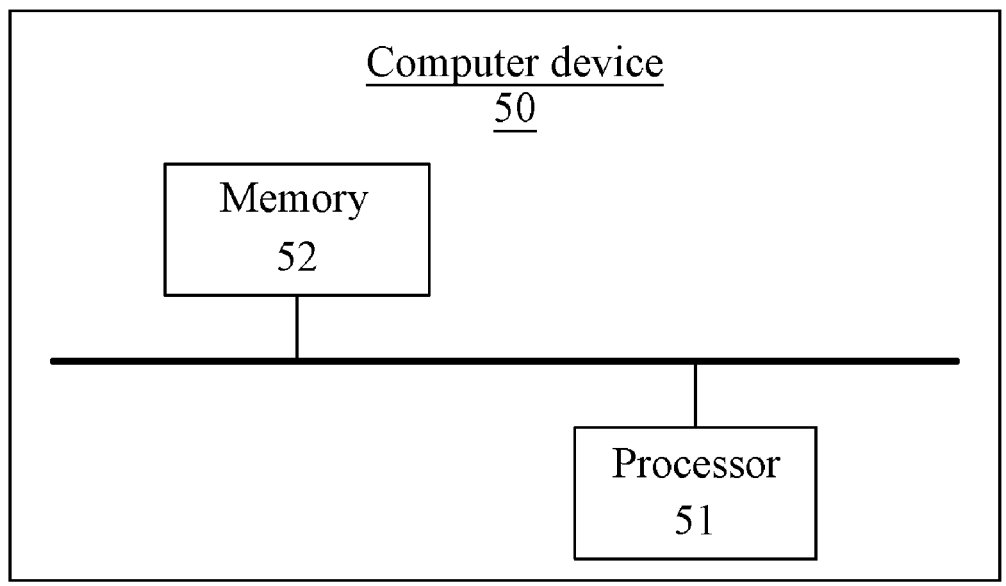
FIG. 4 is a schematic structural diagram of a computer device provided in an embodiment of the present application.

FIG. 4 shows a schematic structural diagram of the computer device provided in the embodiment of the present application. The computer device 50 includes: at least one processor 51 and a memory 52;

the memory stores a computer program; the at least one processor executes the computer program stored in the memory to implement the method provided in the above embodiments.

According to the computer device in the present embodiment, an acoustic characteristic parameter of target tissue is determined according to a target ultrasonic signal of a dynamic broadband corresponding to the target tissue, and an assessment is performed to the target tissue based on the acoustic characteristic parameter of the target tissue. Ultrasonic signals of the target tissue at multiple frequencies are comprehensively considered, so that signal components are varied, thereby improving accuracy of the assessment to the target tissue.

Sixth Embodiment

The present embodiment provides a computer-readable storage medium, where the computer-readable storage medium stores a computer program, and the computer program, when being executed, implements the method provided in any one of the above embodiments.

According to the computer-readable storage medium in the present embodiment, an acoustic characteristic parameter of target tissue is determined according to a target ultrasonic signal of a dynamic broadband corresponding to the target tissue, and an assessment is performed to the target tissue based on the acoustic characteristic parameter of the target tissue. Ultrasonic signals of the target tissue at multiple frequencies are comprehensively considered, so that signal components are varied, thereby improving accuracy of the assessment to the target tissue.

In several embodiments provided in the present application, it should be understood that the disclosed apparatus and method may be implemented in other ways. For example, the apparatus embodiments described above are only illustrative. For example, the division of the units is only a logical function division, and there may be other ways of division in actual implementation, for example, multiple units or components may be combined or integrated into another system, or some features may be ignored or not executed. On the other hand, the mutual coupling or direct coupling or communication connection shown or discussed may be indirect coupling or communication connection through some interfaces, apparatuses or units, and may be in electrical, mechanical or other forms.

The units described as separate components may or may not be physically separated, and the components displayed as units may or may not be physical units, that is, they may be located in one place or distributed to multiple network units. Some or all units can be selected according to actual needs to achieve the purpose of the present embodiment.

In addition, various functional units in the embodiments of the present application may be integrated in one processing unit, and various units may exist separately physically, or two or more units may be integrated in one unit. The above-mentioned integrated units may be implemented in the form of hardware or hardware plus software functional units.

The above-mentioned integrated units realized in the form of software functional units may be stored in a computer-readable storage medium. The above-mentioned software functional unit is stored in a storage medium, including several instructions to cause a computer device (which may be a personal computer, a server, a network device, etc.) or a processor to perform some steps of the methods described in various embodiments of the present application. The aforementioned storage medium includes: a U disk, a removable hard disk, a read-only memory (ROM), a random access memory (RAM), a magnetic disk or an optical disk and other media that can store program code.

Those skilled in the art can clearly understand that for the convenience and brevity of the description, only the division of various functional modules mentioned above is illustrated. In practical application, the above-mentioned functional allocation may be completed by different functional modules according to needs, that is, the internal structure of the apparatus is divided into different functional modules to complete all or part of the functions described above. For the specific working process of the above-described apparatus, reference may be made to the corresponding process in the above-mentioned method embodiment, and will not be repeated here.

Finally, it should be noted that the above embodiments are only used to illustrate the technical solution of the present application, but not to limit it; although the present application has been described in detail with reference to the foregoing embodiments, those of ordinary skills in the art should understand that it is still possible to modify the technical solutions described in the foregoing embodiments or to replace some or all of their technical features equivalently; however, these modifications or substitutions do not make the essence of the corresponding technical solutions deviate from the scope of the technical solutions of various embodiments of the present application.

What is claimed is:

1. An ultrasonic signal processing method, comprising:
   acquiring a target ultrasonic signal of a dynamic broadband corresponding to detection of target tissue, wherein the target ultrasonic signal of the dynamic broadband refers to an ultrasonic signal obtained by a broadband probe to detect the target tissue under excitation of different center frequencies;
   determining an acoustic characteristic parameter of the target tissue according to the target ultrasonic signal; and
   performing assessment processing to the target tissue according to the acoustic characteristic parameter of the target tissue,
   wherein the target ultrasonic signal comprises a signal of at least two frequencies, the acoustic characteristic parameter of the target tissue comprises at least one of a scattering coefficient, a scatterer size, a scatterer distribution, comprehensive information, amplitude variation and frequency variation,
   wherein the amplitude variation refers to amplitude characteristics at different positions, the frequency variation refers to frequency characteristics at different positions, a set of acoustic characteristic parameters is generated for the signal of each frequency, and the comprehensive information refers to information obtained by comprehensively considering a plurality of sets of acoustic characteristic parameters corresponding to a plurality of frequencies.

2. The method according to claim 1, wherein
the determining an acoustic characteristic parameter of the target tissue according to the target ultrasonic signal comprises:
performing, for the signal of each frequency, amplitude extraction to the signal of the frequency to obtain a spatial distribution of amplitude corresponding to the frequency, and adopting, according to the spatial distribution of amplitude corresponding to the frequency, a preset first ultrasonic scattering model to obtain the acoustic characteristic parameter of the target tissue at the frequency.

3. The method according to claim 1, wherein
the determining an acoustic characteristic parameter of the target tissue according to the target ultrasonic signal comprises:
performing, for the signal of each frequency, amplitude extraction to the signal of the frequency to obtain a histogram corresponding to the signal of the frequency, and adopting, according to the histogram corresponding to the signal of the frequency, a preset second ultrasonic scattering model to obtain the acoustic characteristic parameter of the target tissue at the frequency.

4. The method according to claim 1, wherein the performing assessment processing to the target tissue according to the acoustic characteristic parameter of the target tissue comprises:
determining a state of the target tissue according to the acoustic characteristic parameter of the target tissue, wherein the state comprises a normal state and an abnormal state.

5. The method according to claim 1, wherein the target ultrasonic signal is B-mode ultrasonic signals corresponding to the target tissue at different frequencies; and
the determining an acoustic characteristic parameter of the target tissue according to the target ultrasonic signal comprises:
adopting, for a B-mode ultrasonic signal corresponding to the target tissue at each frequency, a preset third ultrasonic scattering model to obtain the acoustic characteristic parameter of the target tissue at the frequency.

6. The method according to claim 1, wherein the target tissue is liver tissue, muscle tissue, adipose tissue, breast tissue or thyroid tissue.

7. An ultrasonic signal processing apparatus, comprising at least one processor and a memory;
the memory storing a computer program; the at least one processor executing the computer program stored in the memory to:
acquire a target ultrasonic signal of a dynamic broadband corresponding to detection of target tissue, wherein the target ultrasonic signal of the dynamic broadband refers to an ultrasonic signal obtained by a broadband probe to detect the target tissue under excitation of different center frequencies;
determine an acoustic characteristic parameter of the target tissue according to the target ultrasonic signal; and
perform assessment processing to the target tissue according to the acoustic characteristic parameter of the target tissue,
wherein the target ultrasonic signal comprises a signal of at least two frequencies, the acoustic characteristic parameter of the target tissue comprises at least one of a scattering coefficient, a scatterer size, a scatterer distribution, comprehensive information, amplitude variation and frequency variation,
wherein the amplitude variation refers to amplitude characteristics at different positions, the frequency variation refers to frequency characteristics at different positions, a set of acoustic characteristic parameters is generated for the signal of each frequency, and the comprehensive information refers to information obtained by comprehensively considering a plurality of sets of acoustic characteristic parameters corresponding to a plurality of frequencies.

8. The apparatus according to claim 7, wherein
the processor is configured to:
perform, for the signal of each frequency, amplitude extraction to the signal of the frequency to obtain a spatial distribution of amplitude corresponding to the frequency, and adopt, according to the spatial distribution of amplitude corresponding to the frequency, a preset first ultrasonic scattering model to obtain the acoustic characteristic parameter of the target tissue at the frequency.

9. The apparatus according to claim 7, wherein
the processor is configured to:
perform, for the signal of each frequency, amplitude extraction to the signal of the frequency to obtain a histogram corresponding to the signal of the frequency, and adopt, according to the histogram corresponding to the signal of the frequency, a preset second ultrasonic scattering model to obtain the acoustic characteristic parameter of the target tissue at the frequency.

10. The apparatus according to claim 7, wherein the processor is configured to:
determine a state of the target tissue according to the acoustic characteristic parameter of the target tissue, wherein the state comprises a normal state and an abnormal state.

11. The apparatus according to claim 7, wherein the target ultrasonic signal is B-mode ultrasonic signals corresponding to the target tissue at different frequencies;
the processor is configured to:
for a B-mode ultrasonic signal corresponding to the target tissue at each frequency, adopt a preset third ultrasonic scattering model to obtain the acoustic characteristic parameter of the target tissue at the frequency.

12. The apparatus according to claim 7, wherein the target tissue is liver tissue, muscle tissue, adipose tissue, breast tissue or thyroid tissue.

13. A non-transitory computer-readable storage medium, wherein the non-transitory computer-readable storage medium stores a computer program and the computer program, when being executed, causes a processor to:
acquire a target ultrasonic signal of a dynamic broadband corresponding to detection of target tissue, wherein the target ultrasonic signal of the dynamic broadband refers to an ultrasonic signal obtained by a broadband probe to detect the target tissue under excitation of different center frequencies;
determine an acoustic characteristic parameter of the target tissue according to the target ultrasonic signal; and
perform assessment processing to the target tissue according to the acoustic characteristic parameter of the target tissue,
wherein the target ultrasonic signal comprises a signal of at least two frequencies, the acoustic characteristic parameter of the target tissue comprises at least one of a scattering coefficient, a scatterer size, a scatterer distribution, comprehensive information, amplitude variation and frequency variation, wherein the amplitude variation refers to amplitude characteristics at different positions, the frequency variation refers to frequency characteristics at different positions, a set of acoustic characteristic parameters is generated for the signal of each frequency, and the comprehensive information refers to information obtained by comprehensively considering a plurality of sets of acoustic characteristic parameters corresponding to a plurality of frequencies.

14. The non-transitory computer-readable storage medium according to claim 13, wherein the processor is configured to:

perform, for the signal of each frequency, amplitude extraction to the signal of the frequency to obtain a spatial distribution of amplitude corresponding to the frequency, and adopt, according to the spatial distribution of amplitude corresponding to the frequency, a preset first ultrasonic scattering model to obtain the acoustic characteristic parameter of the target tissue at the frequency.

15. The non-transitory computer-readable storage medium according to claim 13, wherein the processor is configured to:

perform, for the signal of each frequency, amplitude extraction to the signal of the frequency to obtain a histogram corresponding to the signal of the frequency, and adopt, according to the histogram corresponding to the signal of the frequency, a preset second ultrasonic scattering model to obtain the acoustic characteristic parameter of the target tissue at the frequency.

16. The non-transitory computer-readable storage medium according to claim 13, wherein the processor is configured to:

determine a state of the target tissue according to the acoustic characteristic parameter of the target tissue, wherein the state comprises a normal state and an abnormal state.

17. The non-transitory computer-readable storage medium according to claim 13, wherein the target ultrasonic signal is B-mode ultrasonic signals corresponding to the target tissue at different frequencies;

the processor is configured to:

for a B-mode ultrasonic signal corresponding to the target tissue at each frequency, adopt a preset third ultrasonic scattering model to obtain the acoustic characteristic parameter of the target tissue at the frequency.

* * * * *